United States Patent
Norris et al.

(10) Patent No.: US 9,468,547 B2
(45) Date of Patent: Oct. 18, 2016

(54) DEPLOYMENT OF ENDOLUMINAL DEVICES

(75) Inventors: Patrick M. Norris, Bellemont, AZ (US); Stephanie M. Walsh, Flagstaff, AZ (US); Anthony P. Peterson, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 156 days.

(21) Appl. No.: 13/293,933

(22) Filed: Nov. 10, 2011

(65) Prior Publication Data

US 2012/0130473 A1    May 24, 2012

Related U.S. Application Data (60) Provisional application No. 61/412,647, filed on Nov. 11, 2010.

(51) Int. Cl.
    *A61F 2/06*      (2013.01)
    *A61F 2/97*      (2013.01)
    *A61F 2/82*      (2013.01)

(52) U.S. Cl.
    CPC . *A61F 2/97* (2013.01); *A61F 2/82* (2013.01); *A61F 2250/001* (2013.01); *Y10T 29/49826* (2015.01); *Y10T 29/49947* (2015.01)

(58) Field of Classification Search
    CPC ....... A61F 2220/001; A61F 2/82; A61F 2/97
    USPC ...... 606/108, 191, 194, 200; 623/1.11, 1.12, 623/1.22; 29/525.01
    See application file for complete search history.

(56) References Cited

U.S. PATENT DOCUMENTS

| | | |
|---|---|---|
| 4,406,656 A | 9/1983 | Hattler et al. |
| 4,738,666 A | 4/1988 | Fuqua |
| 5,106,368 A | 4/1992 | Uldall et al. |
| 5,472,418 A | 12/1995 | Palestrant |
| 5,531,717 A | 7/1996 | Roberto et al. |
| 5,569,219 A | 10/1996 | Hakki et al. |
| 5,618,267 A | 4/1997 | Palestrant |
| 5,676,688 A | 10/1997 | Jaker et al. |
| 5,711,841 A | 1/1998 | Jaker |
| 5,807,311 A | 9/1998 | Palestrant |
| 5,827,243 A | 10/1998 | Palestrant |
| 5,868,708 A | 2/1999 | Hart et al. |
| 5,873,906 A * | 2/1999 | Lau ..................... A61F 2/07 128/898 |
| 5,897,535 A | 4/1999 | Feliziani et al. |
| 6,007,488 A | 12/1999 | Jaker et al. |
| 6,096,013 A | 8/2000 | Hakky et al. |
| 6,224,627 B1 * | 5/2001 | Armstrong et al. ......... 623/1.23 |

(Continued)

FOREIGN PATENT DOCUMENTS

| | | |
|---|---|---|
| JP | 08509899 A | 10/1996 |
| JP | 2000-149537 | 5/2000 |

(Continued)

*Primary Examiner* — Corrine McDermott
*Assistant Examiner* — Sarah Simpson (57) ABSTRACT

A catheter assembly includes a single sleeve that constrains an expandable device to a dimension suitable for endoluminal delivery of the device to a treatment site, and further allows expansion of the device toward an outer peripheral dimension that is smaller than a fully deployed outer peripheral dimension to allow positioning of the device at the treatment site prior to full deployment and expansion of the device at the treatment site.

8 Claims, 7 Drawing Sheets

(56) References Cited

U.S. PATENT DOCUMENTS

| | | |
|---|---|---|
| 6,240,968 B1 | 6/2001 | Bigonzi-Jaker et al. |
| 6,352,561 B1 | 3/2002 | Leopold et al. |
| 6,926,509 B2 | 8/2005 | Nicora et al. |
| 7,192,439 B2 | 3/2007 | Khairkhahan et al. |
| 7,235,093 B2 | 6/2007 | Gregorich |
| 7,255,687 B2 | 8/2007 | Huang et al. |
| 7,329,275 B2 | 2/2008 | Yee |
| 7,356,725 B2 | 4/2008 | Engler et al. |
| 7,425,202 B2 | 9/2008 | Huang et al. |
| 7,462,183 B2 | 12/2008 | Behl et al. |
| 7,727,163 B2 | 6/2010 | Behl |
| 7,967,798 B2 | 6/2011 | Reydel et al. |
| 2005/0131523 A1 | 6/2005 | Bashiri et al. |
| 2005/0137688 A1 | 6/2005 | Salahieh et al. |
| 2005/0154443 A1* | 7/2005 | Linder et al. ............... 623/1.11 |
| 2005/0197595 A1 | 9/2005 | Huang et al. |
| 2005/0197627 A1 | 9/2005 | Huang et al. |
| 2006/0009784 A1 | 1/2006 | Behl et al. |
| 2006/0015171 A1* | 1/2006 | Armstrong ............... 623/1.12 |
| 2006/0020319 A1 | 1/2006 | Kim et al. |
| 2006/0064151 A1 | 3/2006 | Guterman et al. |
| 2006/0122566 A1 | 6/2006 | Huang et al. |
| 2006/0173525 A1 | 8/2006 | Behl et al. |
| 2006/0178722 A1 | 8/2006 | Jaker et al. |
| 2006/0229704 A1 | 10/2006 | Thistle et al. |
| 2006/0259122 A1 | 11/2006 | Eliseev |
| 2007/0021820 A1 | 1/2007 | Sisken |
| 2007/0106233 A1 | 5/2007 | Huang et al. |
| 2010/0094401 A1 | 4/2010 | Kolbel et al. |

FOREIGN PATENT DOCUMENTS

| | | |
|---|---|---|
| JP | 2001-47102 | 2/2001 |
| JP | 2001-85024 | 3/2001 |
| JP | 2002518086 A | 6/2002 |
| JP | 2003521971 A | 7/2003 |
| JP | 2007534367 A | 11/2007 |
| JP | 2008506459 A | 3/2008 |
| WO | 92/21399 | 12/1992 |
| WO | 2008047092 A1 | 4/2008 |
| WO | 2008/121380 | 10/2008 |

* cited by examiner

DEPLOYMENT OF ENDOLUMINAL DEVICES

CROSS REFERENCE TO RELATED APPLICATIONS

This application is a non-provisional of, and claims priority to, U.S. Provisional Patent Application No. 61/412,647, entitled "Deployment of Endoluminal Devices," filed Nov. 11, 2010, the content of which is hereby incorporated by reference in its entirety.

BACKGROUND

1. Field

The present disclosure relates to the transcatheter delivery and remote deployment of implantable medical devices and, more particularly, implantable intraluminal devices of either the self-expanding type or the balloon expandable type.

2. Discussion of the Related Art

Endoluminal therapies typically involve the insertion of a delivery catheter that transports an implantable prosthetic device into the vasculature through a small, often percutaneous, access site in a remote vessel. Once access to the vasculature is achieved, the delivery catheter is used to mediate intraluminal delivery and subsequent deployment of the prosthesis via one of several techniques. In this fashion, the prosthesis can be remotely implanted to achieve a therapeutic outcome. In contrast to conventional surgical therapies, endoluminal treatments are distinguished by their "minimally invasive" nature.

Expandable endoprostheses are generally comprised of a stent component with or without a graft covering over the stent interstices. They are designed to spontaneously dilate (i.e., elastically recover) or to be balloon-expanded from their delivery diameter, through a range of intermediary diameters, up to a maximal, pre-determined functional diameter. The endoluminal delivery and deployment of expandable endoprostheses pose several unique problems. First, the endoprosthesis itself must be radially compacted to a suitable introductory size (or delivery diameter) to allow insertion into the vasculature, then it must be constrained in that compacted state and mounted onto a delivery device such as a catheter shaft. Subsequently, the constraint must be removed in order to allow the endoprosthesis to expand to its functional diameter and achieve the desired therapeutic outcome. A variety of ways of constraining and releasing an expandable device are known in the art.

It remains desirable to provide improved systems for endoluminal delivery of stents or stent grafts to vascular treatment sites.

DETAILED DESCRIPTION

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting. Finally, although the present disclosure can be described in connection with various principles and beliefs, the present disclosure should not be bound by theory.

Throughout this specification and in the claims, the term "distal" can refer to a location that is, or a portion of an intraluminal device (such as a stent-graft) that when implanted is, further downstream with respect to blood flow than another portion of the device. Similarly, the term "distally" can refer to the direction of blood flow or further downstream in the direction of blood flow.

The term "proximal" can refer to a location that is, or a portion of an intraluminal device that when implanted is, further upstream with respect to blood flow. Similarly, the term "proximally" can refer to the direction opposite to the direction of blood flow or upstream from the direction of blood flow.

With further regard to the terms proximal and distal, and because the present disclosure is not limited to peripheral and/or central approaches, this disclosure should not be narrowly construed with respect to these terms. Rather, the devices and methods described herein can be altered and/or adjusted relative to the anatomy of a patient.

In various embodiments, a catheter assembly is disclosed which utilizes a single flexible sleeve that releasably maintains an expandable device, such as an expandable endoluminal graft, to a dimension suitable for endoluminal delivery of the device to a treatment site, such as a vascular member in a patient's body; and further limits expansion of the device to an outer peripheral dimension that is smaller than an unconstrained or fully deployed outer peripheral dimension thereby facilitating selective axial and/or rotational positioning of the device at the treatment site prior to full deployment and expansion of the device toward engagement with inner walls of the vasculature at the treatment site.

Figure 1:
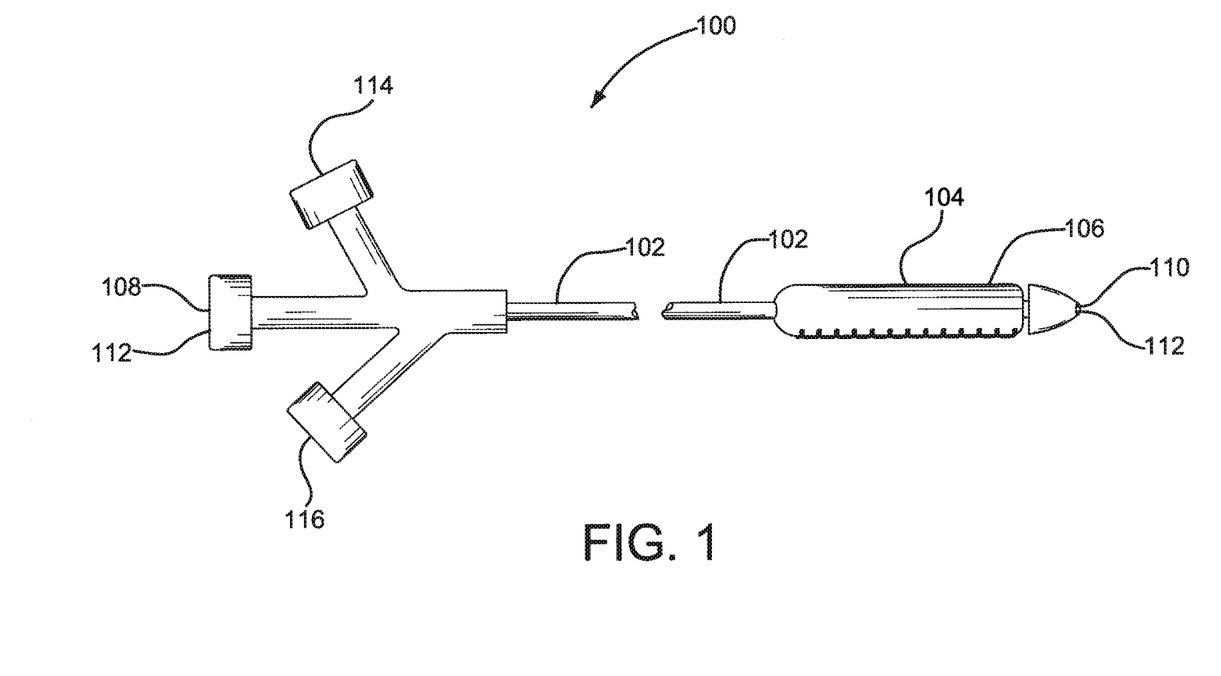
FIG. 1 is a side view of a catheter assembly having a compacted and constrained medical device near a distal end of the catheter.

In various embodiments, for example as shown in FIG. 1, the catheter assembly, which is generally indicated at 100, includes a catheter 102, an expandable device 104 and a restraining member or flexible sleeve 106. The catheter 102 extends longitudinally and has opposite proximal 110 and distal 108 ends. The catheter 102 also includes a lumen 112 extending between the proximal 110 and distal 108 ends.

The expandable device 104 is disposed at or near the proximal end 110 of the catheter 102. The device 104 is expandable to engage surrounding tissue at the treatment site, such as inner surfaces of a vascular member. The device 104 can include a self-expanding nitinol frame that expands the device 104 upon deployment at the treatment site. The device 104 can also be balloon expandable.

In various embodiments, the flexible sleeve 106 extends around the device 104 and has a first outer peripheral dimension 208, at which the flexible sleeve 106 constrains and releasably maintains the device 104 in a collapsed state or small diameter delivery profile suitable for endoluminal delivery and advancement through typical vasculature to a treatment site. Fully opening the sleeve 106 allows the device 104 to fully expand toward an unconstrained or fully deployed outer peripheral dimension of the device 104, wherein the device 104 is fully expanded and not constrained by the flexible sleeve and/or vasculature. It should be appreciated that the device can be oversized relative to the intended vasculature to be treated to promote engagement between the device and the inner walls of the vasculature at the treatment site.

Figure 2A:
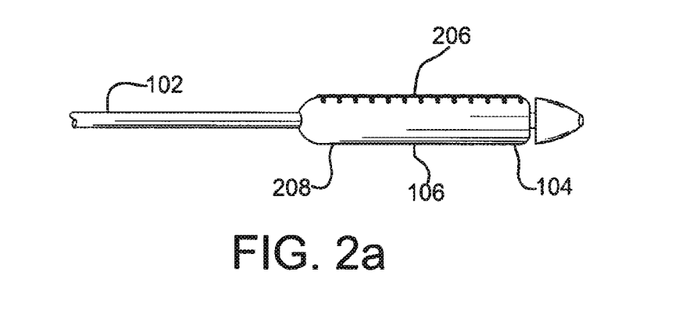
FIGS. 2a through 2c are partial side perspective views of an expandable medical device shown in various stages of deployment.

The flexible sleeve can have various configurations for constraining the sleeve. In various embodiments, the sleeve 106 includes generally opposite portions or edges each with a plurality of openings. The openings are arranged to form stitch lines that extend along the opposite portions of the sleeve 106. The sleeve 106 can extend around the device 104 and the opposite portions brought together to form a releasable seam 206, as shown in FIG. 2a. The releasable seam 206 can be held together by an elongated coupling member extending through or woven through the openings. Examples of coupling members include control tethers, wires, lines, and the like. The control member can extend through a catheter shaft 102 and be accessed through proximal connectors as indicated, for example, at 112, 114 or 116. Tensioning, actuation and displacement of the coupling member from the openings allows the sleeve 106 to open along the seam 206 and the device 104 to expand toward a larger diameter. Examples of restraining members and coupling members for releasably maintaining expandable devices in a collapsed state for endoluminal delivery can be found in U.S. Pat. No. 6,352,561 to Leopold et al, the content of which is incorporated herein by reference in its entirety.

Figure 2B:
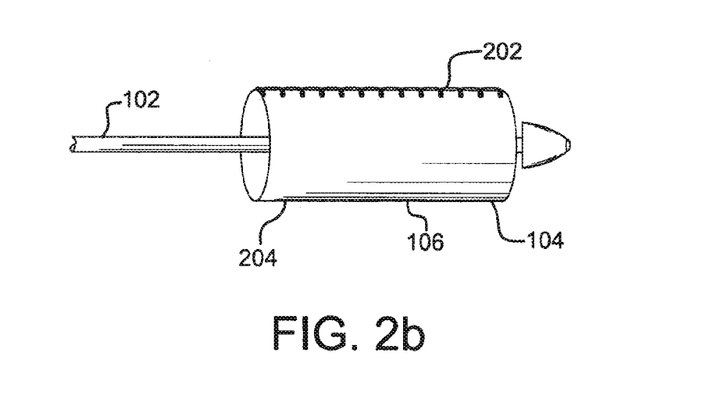

In various embodiments, the flexible sleeve 106 can be configured to maintain the device 104 in an intermediate state, as illustrated in FIG. 2b, in which the sleeve 106 is maintained at a second outer peripheral dimension that is larger than the first outer peripheral dimension of the sleeve 106, yet smaller than the fully deployed outer peripheral dimension of the device 104. Thus, when the device 104 is positioned generally at or near the treatment site, the flexible sleeve 106 can be actuated to allow the sleeve 106 to expand or be pushed outwardly toward the intermediate state by a generally radially outward force applied by expansion of the device 104 by, for example, a balloon and/or by a stent or wire frame portion of the device. Maintaining the device in the intermediate state allows the clinician to adjust the axial and/or rotational position of the device with respect to the vasculature prior to full release and expansion of the device toward the fully deployed outer peripheral dimension and engagement with surrounding vasculature tissue.

In various embodiments, the sleeve is maintained in this intermediate state or second outer peripheral dimension 204 by a second releasable seam 202 held together by a portion of the same coupling member used to secure the first releasable seam or, alternatively, by a separate coupling member separate from the first releasable seam. Thus, in various embodiments, a single flexible sleeve is formed having a multi-stage deployment. In a dual stage configuration, for example, the sleeve can have a first outer peripheral dimension, indicated at 208 in FIG. 2a, releasably maintained by a first releasable seam 206 and a second outer peripheral dimension, indicated at 204 in FIG. 2b, releasably maintained by a second releasable seam 202. In various other embodiments, the sleeve can be formed with more than two states or stages and associated multiple outer peripheral dimensions can be utilized leading toward the final fully deployed outer peripheral dimension by incorporating additional releasable seam arrangements.

Figure 3A:
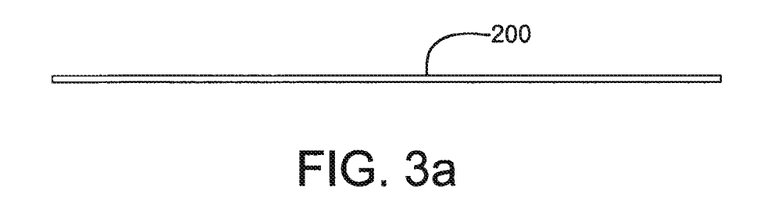
FIGS. 3a through 3c, 3c' and 3c" are side views and perspective views depicting a method of making a flexible constraining sleeve with two releasable seams.
Figure 3B:
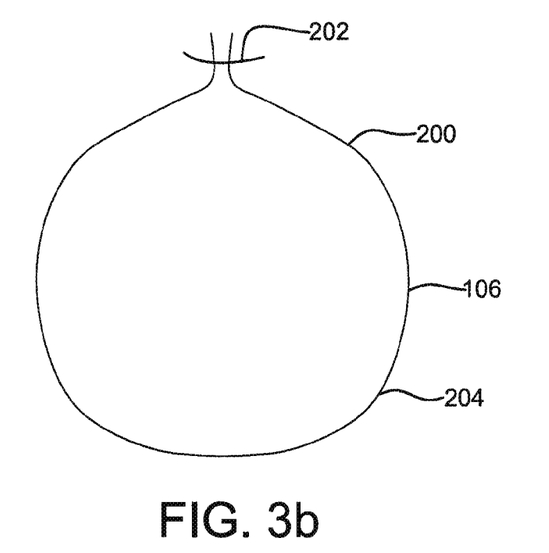
Figure 3C:
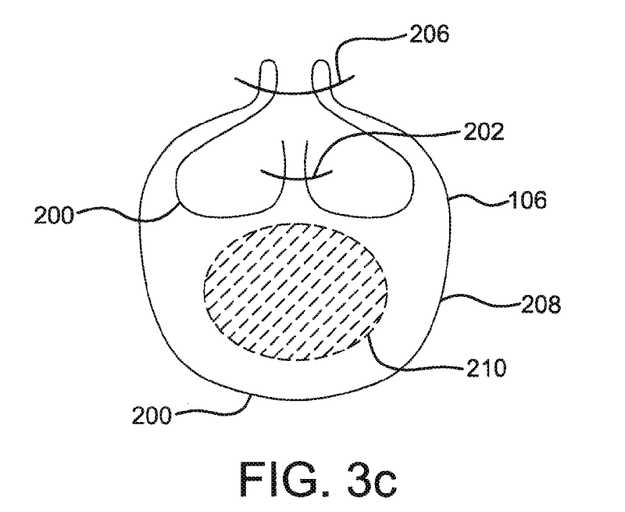

A method of forming a restraining member in accordance with the present disclosure is generally illustrated by the sequence of FIGS. 3a through 3c, in which a restraining member have a multi-stage deployment is formed by interconnecting portions of a flexible sheet together to form a releasable seam to define a lumen with a first outer peripheral dimension and interconnecting other portions of the flexible sheet together to form another releasable seam to reduce the size of the lumen to a second outer peripheral dimension. Shown in FIG. 3a is an edge view of a flexible sheet material 200 that will be subsequently formed into a restraining member. In various embodiments, the sheet can be formed by flattening a tube of flexible material, such as ePTFE, so that the resulting lumen is double-walled.

The sheet 200 is folded over onto itself to form a lumen, as shown in FIG. 3b. Portions or edges of the folded sheet 200 are then stitched with a coupling member to form a releasable seam 202. The resulting lumen limits expansion of the device to the intermediate state, as discussed above.

Other portions of the flexible sheet are then folded and interconnected to form an additional releasable seam 206 to further reduce the size of the lumen to an outer peripheral dimension suitable for endoluminal delivery of the device. The cross sectional area 210 roughly illustrates the area in which the device will be constrained.

The seams 202, 206, as shown in the illustrated embodiment in FIG. 3C, are generally radially aligned or positioned substantially along the same side of the area 210. In various other embodiments, however, the seams can be offset rotationally about the area 210. The seams, for example, can be disposed on opposite sides of the area 210 relative to each other.

To reiterate the delivery sequence, the device (FIG. 1, 104) is initially constrained to a small diameter delivery state as shown in FIG. 2a. The flexible sleeve 106, while in this small diameter state, has a small or first outer peripheral dimension 208 suitable for endoluminal delivery of the device to a treatment site. When the releasable first seam 206 is actuated, the sleeve 106 will expand to a larger diameter state or second outer peripheral dimension 204, as shown in FIG. 2b, due to a generally radially outward force applied by the expansion of the device 104, either by balloon and/or by a stent or wire frame portion of the device. To complete delivery or full deployment of the device at the treatment site, the releasable second seam 202 is actuated which "splits open" the sleeve 106 to allow the device to expand toward the fully deployed outer peripheral dimension and engage surrounding tissue at the treatment site.

In various embodiments, a flexible sleeve used for a constraint can comprise materials similar to those used to form a graft. In various other embodiments, the precursor flexible sheet (FIG. 2a, 200) can be formed from a flattened, thin wall tube. A thin wall tube (as well as a sheet) can incorporate "rip-stops" in the form of longitudinal high strength fibers attached or embedded into the sheet or tube wall.

To allow manipulation and repositioning of the partially expanded device via a catheter, the device, in various embodiments, is releasably coupled to the catheter. In various embodiments, a partially or fully expanded stent or stent graft may be releasably coupled to a catheter by, for example, removable tie-lines, clips and the like.

Figure 4A:
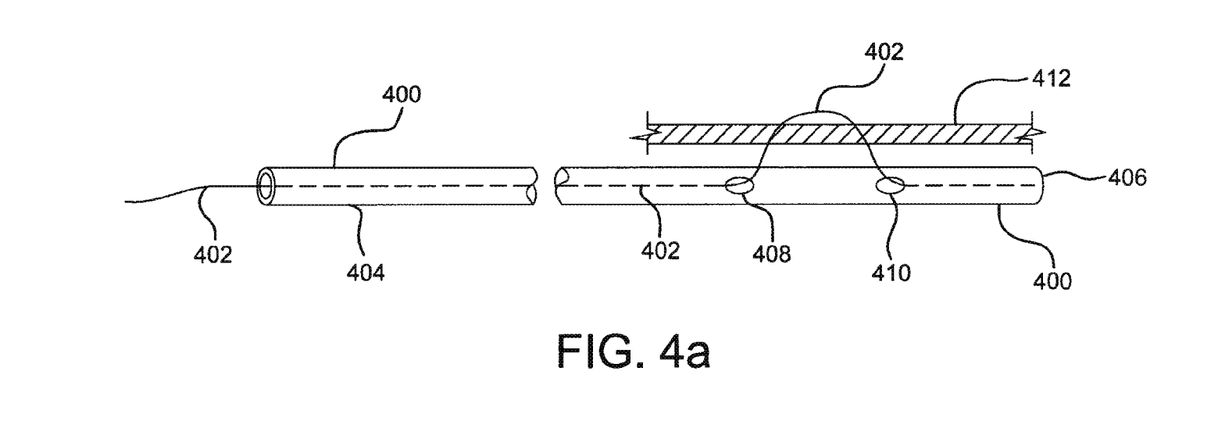
FIGS. 4a through 4c are side views and a perspective view of a lock wire for releasably coupling the medical device to the catheter.
Figure 4B:
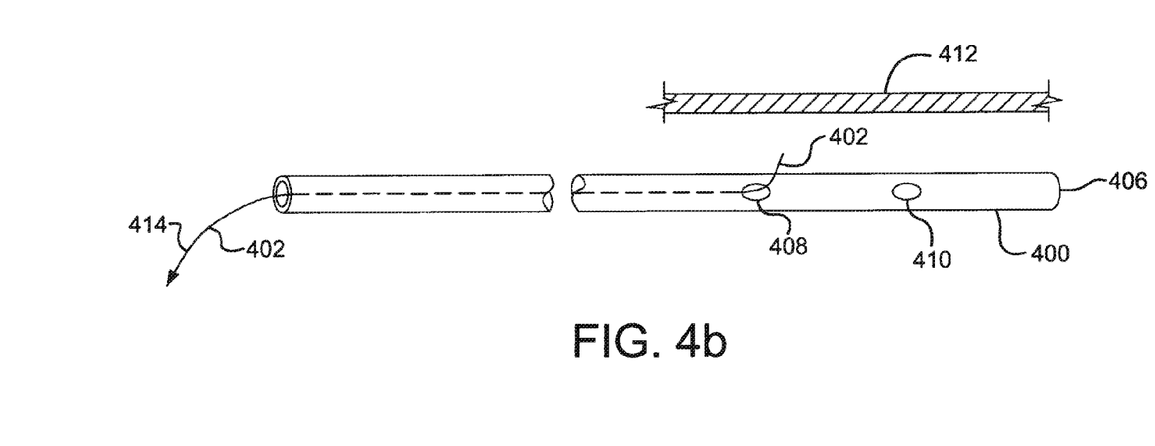
Figure 4C:
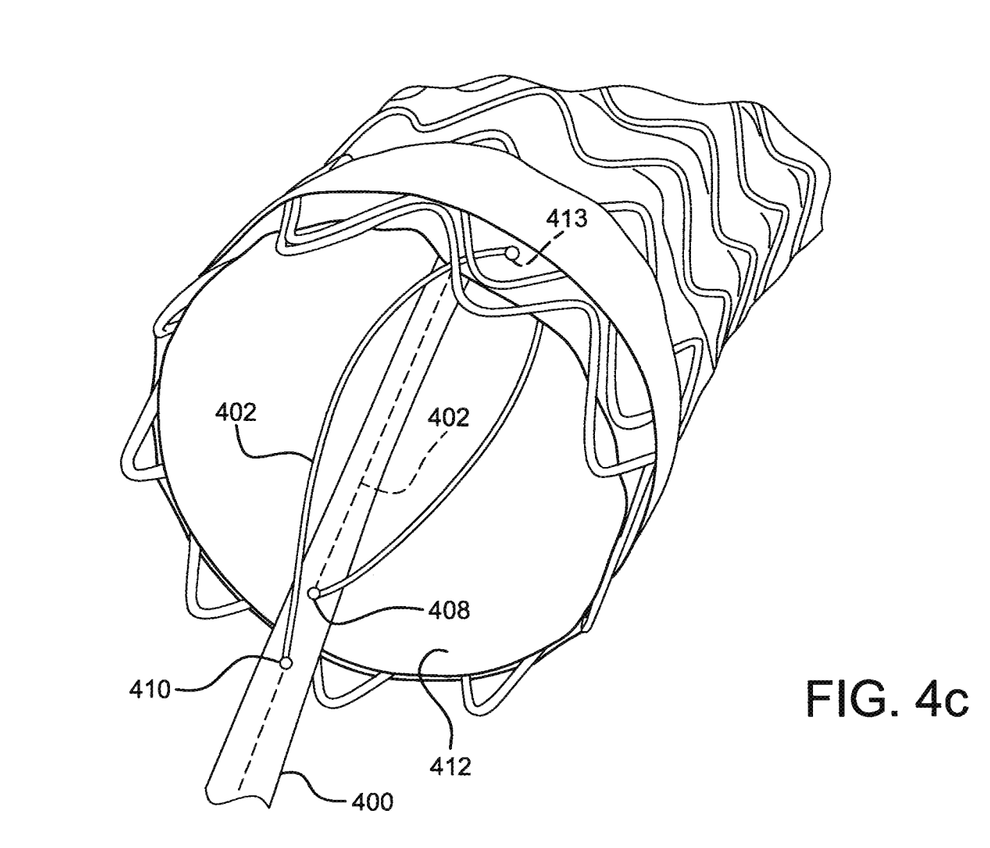

In other embodiments, as shown in FIGS. 4a and 4c, a catheter shaft 400 having generally opposite distal 404 and proximal ends 406 is positioned adjacent a stent graft wall 412, either internally or externally with respect to the stent graft. To releasably couple the catheter shaft 400 to the stent graft wall 412, an elongated member 402, such as a wire, can extend through a distal end 404 of the catheter shaft 400. The elongated member 402 can further extend through the catheter lumen and extend outwardly through a distal side wall opening 408. The elongated member can form a loop, penetrating the graft wall 412 through at least one aperture 413 in the graft wall 412 and returning into the catheter lumen through a proximal side wall opening 410. The elongated member 402 is, by this arrangement, releasably coupled to the graft wall, allowing manipulation and repositioning of the graft as required. Alternatively, the elongated member can extend through an apice of a wire frame or at least extend around a portion of the wire frame to releasably couple the catheter shaft to the stent graft wall.

When the graft is positioned at a desired location along the treatment site, the catheter 400 can be disengaged from the graft wall 412 to allow removal of the catheter from the treatment site and allow the stent graft to remain in place at the treatment site. More specifically, as shown in FIG. 4b, the catheter can be released from the graft wall by retracting the elongated member 402 in a distal direction as depicted by direction arrow 414. The elongated member can exit both catheter side wall holes 408, 410 and be fully withdrawn from the catheter lumen.

An elongated member 402, as shown in FIG. 4b, can be threaded through a graft wall, through a stent frame or through a graft/stent coupling element such as a hook. In various embodiments, elongated members can also be attached to a graft through a "cork-screw" configuration. Such a cork-screw can be twisted to engage and penetrate a graft wall (or lock to a stent frame) and be un-twisted to release the elongated member from the graft/stent.

Elongated members or lock wires, in various embodiments, can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol. In other various embodiments, elongated members or lock wires can also be formed from high strength polymer fibers such as ultra high molecular weight polyethylene fibers (e.g., Spectra®, Dyneema Purity®, etc.) or aramid fibers (e.g., Technora®, etc.).

Figure 2C:
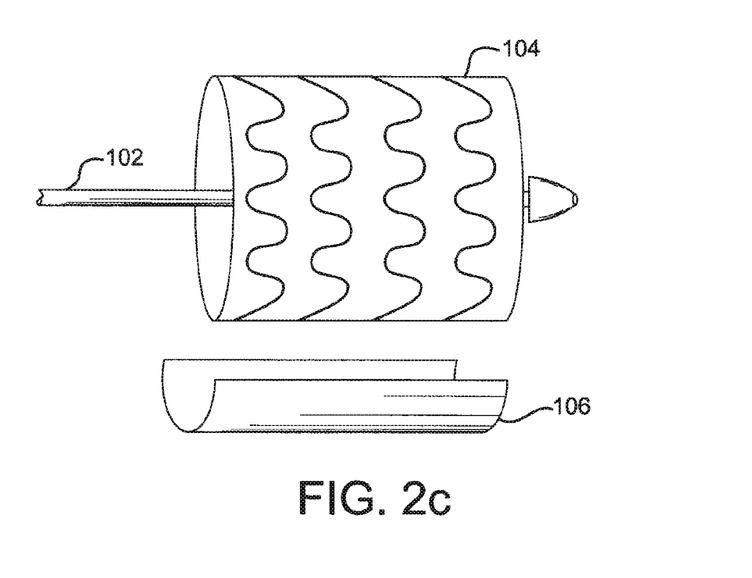

When the graft is positioned at a desired location along the treatment site, the flexible sleeve 106 can be further actuated to allow the sleeve 106 to "split open" and fully release the device 104, as illustrated in FIG. 2c. The device 104 can then expand toward the fully deployed outer peripheral dimension and engage the vascular wall. Referring back to FIG. 4b, the catheter can be released from the graft wall of the now-deployed device 104 by retracting the elongated member 402 in a distal direction as depicted by direction arrow 414. The elongated member can exit both catheter side wall holes 408, 410 and be fully withdrawn from the catheter lumen.

Stents can have various configurations as known in the art and can be fabricated, for example, from cut tubes, wound wires (or ribbons) or flat patterned sheets rolled into a tubular form. Stents can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stents can also comprise bioresorbable materials such as poly(amino acids), poly(anhydrides), poly(caprolactones), poly(lactic/glycolic acid) polymers, poly(hydroxybutyrates) and poly(orthoesters).

Potential materials for a graft member include, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene, aramid fibers, and combinations thereof. One preferred embodiment for a graft material is ePTFE. Other embodiments for a graft member material can include high strength polymer fibers such as ultra high molecular weight polyethylene fibers (e.g., Spectra®, Dyneema Purity®, etc.) or aramid fibers (e.g., Technora®, etc.). The graft member can include a bioactive agent. In one embodiment, an ePTFE graft includes a carbon component along a blood contacting surface thereof.

Typical materials used to construct catheters can comprise commonly known materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenelyne Ether (PPE), Modified Polyphenelyne Ether (Mod PPE) Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluroethylene (ECTFE), Ethylene, Ethylene Tetrafluoroethylene (ETFE), Polychlortrifluoroethylene (PCTFE), Polytetrafluoroethylene (PTFE), Polyvinylidene Fluoride (PVDF), Periluoroalkoxy (PFA). Other commonly known medical grade materials include elastomeric organosilicon polymers, polyether block amide or thermoplastic copolyether (PEBAX) and metals such as stainless steel and nickel/titanium alloys.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method of forming a catheter assembly, said method comprising:
   releasably coupling an expandable device and a catheter having a length defined between a first end and an opposite second end thereof;
   forming a restraining member by releasably interconnecting opposing portions of a flexible sheet together to form a releasable seam including a first plurality of openings formed along the flexible sheet to maintain the restraining member and device at a first outer peripheral dimension along the length of the device between the first and second ends thereof suitable for endoluminal delivery of the device to a treatment site, and by releasably interconnecting other opposing portions of the flexible sheet together to form another releasable seam, disposed between the catheter and the releasable seam and radially aligned therewith, including a second plurality of openings formed along the flexible sheet to maintain the restraining member and device at a second outer peripheral dimension along the length of the device between the first and second ends thereof that is larger than the first outer peripheral dimension and smaller than a fully deployed outer peripheral dimension.

2. The method as set forth in claim 1 including maintaining each of the releasable seams with an elongated member woven along each of the plurality of openings formed along opposing portions of the flexible sheet.

3. The method as set forth in claim 1 including loading the device in a compacted state in the restraining member and retaining the device in the first outer peripheral dimension.

4. The method as set forth in claim 1 including releasably coupling the device and the catheter by extending an elongated member through the catheter and through a portion of the device.

5. The method as set forth in claim 4 including weaving the elongated member between portions of a graft wall and a stent frame of the device.

6. The method as set forth in claim 5 including loading the device in a compacted state in the restraining member while the device and catheter are releasably coupled by the elongated member and retaining the device in the first outer peripheral dimension.

7. A method of forming a catheter assembly, said method comprising:
   providing a catheter;
   providing an expandable device releasably coupled to the catheter, the expandable device having a first end and an opposite second end, the expandable device having an outer surface and an opposite inner surface defining a flow lumen extending between the first end and second end;
   releasably coupling the expandable device and the catheter;
   forming a restraining member by releasably interconnecting opposing portions of a flexible sheet together to form a first releasable seam including a first plurality of openings formed along the flexible sheet to maintain the restraining member and a full length of the expandable device at a first outer peripheral dimension suitable for endoluminal delivery of the expandable device to a treatment site, and by releasably interconnecting other opposing portions of the flexible sheet together to form a second releasable seam, disposed between the catheter and the first releasable seam and radially aligned therewith, including a second plurality of openings formed along the flexible sheet to maintain the full length of the expandable device at a second outer peripheral dimension larger than the first outer peripheral dimension and smaller than a fully deployed outer peripheral dimension to allow blood flow through the flow lumen and to allow positioning of the expandable device after release of the first releasable seam and prior to release of the second releasable seam.

8. The method as set forth in claim 7, wherein the restraining member maintains the expandable device at the second outer peripheral dimension between the first and second ends after release of the first releasable seam.

* * * * *